United States Patent
Kawai et al.

(10) Patent No.: US 7,518,025 B2
(45) Date of Patent: Apr. 14, 2009

(54) PROCESS FOR PRODUCING ALKYL AROMATIC COMPOUND

(75) Inventors: Takeshi Kawai, Ibaraki (JP); Kenji Inamasa, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/532,709

(22) PCT Filed: Oct. 29, 2003

(86) PCT No.: PCT/JP03/13842
§ 371 (c)(1),
(2), (4) Date: Apr. 27, 2005

(87) PCT Pub. No.: WO2004/039756
PCT Pub. Date: May 13, 2004

(65) Prior Publication Data
US 2006/0122439 A1 Jun. 8, 2006

(30) Foreign Application Priority Data
Nov. 1, 2002 (JP) .............................. 2002-319608

(51) Int. Cl.
*C07C 15/08* (2006.01)
*C07C 15/067* (2006.01)
(52) U.S. Cl. .................. 585/400; 585/446; 585/464; 585/477
(58) Field of Classification Search ................ 585/400, 585/477, 446; 570/127, 202, 190; 568/932, 568/939, 630, 631, 632, 633, 648
See application file for complete search history.

(56) References Cited

U.S. PATENT DOCUMENTS

| | | | | | |
|---|---|---|---|---|---|
| 2,372,320 | A | * | 3/1945 | Frey | 585/323 |
| 2,766,307 | A | * | 10/1956 | McCaulay et al. | 585/464 |
| 2,868,854 | A | * | 1/1959 | Lien et al. | 585/478 |
| 3,766,286 | A | * | 10/1973 | Olah | 585/480 |

FOREIGN PATENT DOCUMENTS

JP 1-319444 12/1989

OTHER PUBLICATIONS

Supplementary European Search Report dated Oct. 6, 2008, for Application No. EP 03 76 9953.

* cited by examiner

*Primary Examiner*—Rosalynd Keys
(74) *Attorney, Agent, or Firm*—Antonelli, Terry, Stout & Kraus, LLP.

(57) ABSTRACT

A process is provided for producing an alkyl aromatic compound having substituents at the 3- and 5-positions by alkylating an aromatic compound having two substituents in the meta positions with an olefin having 2 to 4 carbon atoms in the presence of a Broensted acid, followed by addition of a Lewis acid and isomerization in the copresence of the Broensted acid and the Lewis acid. According to the present invention, 3,5-dimethylethylbenzene, 3,5-dimethylcumene, etc. may be produced in a stable manner with high yield and high selectivity under mild and simple reaction conditions. The alkyl aromatic compounds having substituents at the 3- and 5-positions are useful as intermediates for functional chemicals for use in pharmaceutical, agricultural and electronic materials. With the method of the present invention, the catalyst used can be recovered and recycled. Thus, desired alkyl aromatic compounds may be obtained economically in an industrially advantageous manner while reducing the load on the environment.

15 Claims, No Drawings

PROCESS FOR PRODUCING ALKYL AROMATIC COMPOUND

TECHNICAL FIELD

The present invention relates to a process for the alkylation of an aromatic compound having substituents and, more specifically, to an improved process for producing an alkyl aromatic compound having substituents at the 3- and 5-positions, such as 3,5-dimethylethylbenzene or 3,5-dimethylcumene, by alkylating an aromatic compound having two substituents in the meta positions with a lower olefin such as ethylene or propylene. Such alkyl aromatic compounds are useful as raw materials for pharmaceuticals, agricultural chemicals, liquid crystals, functional pigments, solvents and monomers for engineering plastics.

BACKGROUND ART

As a method for the alkylation of an aromatic compound, a Friedel-Crafts alkylation reaction or a gaseous phase reaction which uses a solid acid catalyst are widely known.

In alkylating an aromatic compound, the position (ortho, meta or para position) of the aromatic ring of the raw material to which an alkyl group is introduced is determined by the effect of the functional group (orientation). When the desired compound is not in accord with the substitution orientation inherent to the functional group, however, a positional isomer of the desired compound is obtained as a product. Therefore, it is necessary to carry out disproportionation called an isomerization reaction or a transalkylation reaction in order to introduce the alkyl group to the desired position.

For example, the Friedel-Crafts alkylation is a method known from the past, in which a Lewis acid catalyst such as aluminum chloride is used as a catalyst. With a method using aluminum chloride as an alkylation agent, the selectivity to a monoalkyl compound in the alkylation reaction is low. Further, the method requires complicated steps of separation of the monoalkylated product from a polyalkylated product by distillation and the subsequent transalkylation of the polyalkyl compound to the monoalkyl compound (JP-A-Sho 57-40419).

JP-A-Hei 04-346939 discloses a method in which alkylation is carried out using aluminum chloride, followed by transalkylation using a solid acid catalyst. This method, however, requires removal or separation by distillation of aluminum chloride and HCl used as a co-catalyst prior to the transalkylation and, therefore, is a complicated multi-step process.

U.S. Pat. No. 5,030,777 discloses a process for producing 3,5-dichloroalkylbenzene in which a dichlorobenzene is subjected to an alkylation reaction using aluminum chloride as a catalyst and isopropyl bromide as an alkylating agent, followed by isomeriziation and transalkylation. This process has problems that a halogenated alkyl must be used as a raw material and that the process steps are complicated.

The Friedel-Crafts alkylation reaction using aluminum chloride requires complicated steps as described above. Further, the amount of the catalyst relative to the raw material is large. Furthermore, the catalyst is apt to be inactivated because the catalyst tends to form a complex with various compounds produced by the reaction. Additionally, in order to separate the product from aluminum chloride after termination of the reaction, it is necessary to treat the reaction mixture with water. As a consequence of the treatment, aluminum chloride turns into aluminum hydroxide. Thus, the method has a defect that it is difficult to recycle the catalyst.

With regard to the alkylation reaction using other Lewis acids, U.S. Pat. No. 4,943,668 discloses an alkylation reaction of metaxylene using aluminum halide and iodine as a catalyst and an α-olefin as an alkylating agent. This method, however, has defects that iodine should be used in addition to aluminum halide and that the reaction time is as long as 2 to 7 hours. U.S. Pat. No. 4,048,248 discloses a method of alkylating an aromatic compound using titanium tetrafluoride. With this method, the selectivity to the desired product is 60 to 70% and is not satisfactory.

JP-A-Hei 06-263656 discloses a method in which a rare earth-containing catalyst using a perfluoroalkyl group-containing sulfonyl group as a counter anion is used. This method is superior in comparison with a method using an aluminum halide catalyst, since the catalyst may be recycled. However, this method has problems that the catalyst is expensive and that the selectivity is low due to accompanying polyalkylation reaction. Namely, the yield of mono-substituted products is about 30%, the yield of di-substituted products is about 10 to 30%, and the yield of tri-substituted products is about 10%. U.S. Pat. No. 4,158,677 discloses an example of dialkylating an alkylbenzene using a carboxylic acid complex of $BF_3$ for the production of synthetic oils (lubricants). While the reaction gives a yield of the desired product of as high as about 90%, this method has problems that a long reaction time of 20 hours or more is required and that the post treatment of the reaction liquid is troublesome.

As described above, any conventional alkylation reaction using a Lewis acid as a catalyst has problems. Further, as a common problem in all manufacturing methods, the reaction requires multi-steps and complicated post treatment and, therefore, is ill-suited for industrial production.

Described in the foregoing are alkylation reactions using as a catalyst a Lewis acid represented by aluminum chloride. Also well known is an alkylation reaction using as a catalyst HF which is a Broensted acid. Further, a reaction using HF as an alkylation catalyst is disclosed. This method pertains to a process for producing gasoline having an improved octane number, wherein $C_2$ to $C_{20}$ olefins containing HF and a paraffin are passed through a column having a fixed bed of an inert support. From the object thereof, the product must be a mixture of various compounds. Thus, this method is not considered to pertain to selective alkylation. For example, in the case of trimethylpentane which is the major product, the weight proportion is about 70% and the selectivity is low (U.S. Pat. No. 4,783,567 and No. 4,891,466).

U.S. Pat. No. 2,766,307, No. 2,803,682 and No. 2,803,683 and D. A. McCaulay and A. P. Lien, J. Am. Chem. Soc., 77, 1803 (1955) disclose a method for producing alkylxylenes by ethylation or isopropylation of metaxylene. In the methods disclosed in the above patents and article, the catalyst system uses HF and $BF_3$ at the same time. Further, HF is used in an amount of 10 to 20 moles per mole of the raw material substituted aromatic compound, which is much greater than that in the present invention. Thus, a problem is caused that the efficiency of the separation and purification of HF used as the catalyst and the desired product is low.

As an alkylation method using other acids, there may be mentioned fixed bed alkylation using a fluorinated sulfonic acid catalyst and reaction using a zeolite catalyst (JP-A-Hei 09-2982). However, in the example using a fluorinated sulfonic acid catalyst, the conversion of the raw material aromatic compound is not satisfactory (about 30%). Further, the method has a problem with respect to the selectivity, since branched alkylated products and polyalkylated products are produced. A method disclosed in JP-A-2000-297049 and JP-A-2002-20325 uses zeolite catalysts. While the method is excellent with respect to easiness in separation of the product from the catalyst, polyalkylated products are by-produced in an amount of 10% or more. Additionally, the catalyst is expensive.

DISCLOSURE OF THE INVENTION

In the above circumstances, it is an object of the present invention to provide a process for producing an alkyl aromatic compound having substituents at the 3- and 5-positions by alkylation of an aromatic compound having two substituents at the meta positions, which is high in the yield of and in the selectivity to the desired compound, which permits recovery and recycling of the catalyst and which can be industrially practiced.

The present inventors have made earnest study in view of the foregoing circumstance and have found that the desired alkyl aromatic compound having substituents at the 3- and 5-positions can be obtained in a stable manner with a high yield and a high selectivity under mild and simple reaction conditions by alkylating an aromatic compound having two substituents at the meta positions with an olefin having 2 to 4 carbon atoms in the presence of a Broensted catalyst such as HF, followed by addition of a Lewis acid such as $BF_3$ and permitting intramolecular isomerization to proceed. The present invention has been completed by the above finding.

Thus, the present invention provides the following process for producing an alkyl aromatic compound.

1. A process for producing an alkyl aromatic compound represented by the general formula (2), characterized in that an aromatic compound represented by the general formula (1) is alkylated with an olefin having 2 to 4 carbon atoms in the presence of a Broensted acid, and in that the resulting mixture is subsequently added with a Lewis acid and is subjected to isomerization in the copresence of the Broensted acid and the Lewis acid.

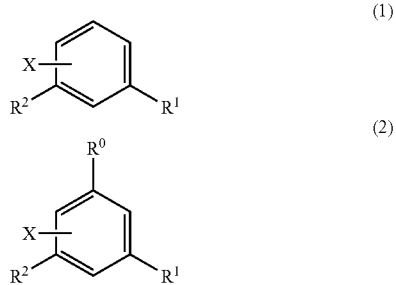

wherein $R^1$ and $R^2$ each independently represent an alkyl group, a perfluoroalkyl group, a halogen atom, a nitro group or an alkyloxy or aryloxy group which may have a substituent, X represents a hydrogen atom, an alkyl group, an aryl group, a perfluoroalkyl group, a halogen atom, a nitro group or an alkyloxy or aryloxy group which may have a substituent, or X may be taken in combination with one or both of the adjacent groups $R^1$ and $R^2$ to represent a cycling structure which may have a substituent, and $R^0$ represents an ethyl group, an isopropyl group, a sec-butyl group or a tert-butyl group.

2. A process for producing an alkyl aromatic compound as recited in 1 above, in which the reaction of the aromatic compound represented by the general formula (1) with the olefin in the presence of a Broensted acid is performed with a molar ratio of the Broensted acid to the aromatic compound being 1 or more.

3. A process for producing an alkyl aromatic compound as recited in 1 or 2 above, in which the reaction of the aromatic compound represented by the general formula (1) with the olefin in the presence of a Broensted acid is performed at a temperature lower than 50° C. but not lower than −30° C.

4. A process for producing an alkyl aromatic compound as recited in any one of 1 through 3 above, in which the isomerization in the copresence of the Lewis acid and the Broensted acid after the reaction of the aromatic compound represented by the general formula (1) with the olefin in the presence of a Broensted acid is performed with a molar ratio of the Lewis acid to the aromatic compound represented by the general formula (1) being 0.5 or more.

5. A process for producing an alkyl aromatic compound as recited in any one of 1 through 4 above, in which the isomerization in the copresence of the Lewis acid and the Broensted acid after the reaction of the aromatic compound represented by the general formula (1) with the olefin in the presence of a Broensted acid is performed at a temperature lower than 50° C. but not lower than −30° C.

6. A process for producing an alkyl aromatic compound as recited in any one of 1 through 5 above, in which the Broensted acid is HF and the Lewis acid is $BF_3$.

7. A process for producing an alkyl aromatic compound as recited in any one of 1 through 6 above, in which the olefin having 2 to 4 carbon atoms is selected from the group consisting of ethylene, propylene, butylenes and isobutylene.

8. A process for producing an alkyl aromatic compound as recited in any one of 1 through 7 above, in which $R^1$ and $R^2$ are each a methyl group and X is a hydrogen atom in the general formulas (1) and (2), and in which $R^0$ is an isopropyl group in the general formula (2).

BEST MODE FOR CARRYING OUT THE INVENTION

The present invention will be described in detail below. In the present invention, the aromatic compound represented by the above general formula (1) is first reacted with an olefin having 2 to 4 carbon atoms and serving as an alkylating agent in the presence of a Broensted acid such as HF to form an alkylated aromatic compound.

As the olefin having 2 to 4 carbon atoms, there may be mentioned ethylene, propylene, butylenes, isobutylene, etc. It is preferred that the olefin be used in an amount of 0.5 to 1 mole per mole of the aromatic compound represented by the formula (1). The use of the olefin in an amount of 0.5 to 1 mole is industrially advantageous because the selectivity based on the olefin is good.

The Broensted acid used in the alkylation reaction is preferably HF for reasons of strong acidity, easiness in recovery and separation, and homogeneity of the complex thereof with a Lewis acid. A Lewis acid which forms a complex with HF hinders the alkylation reaction and, therefore, should not be used in the alkylation stage. The amount of HF must be at least 1 mole, preferably 2 to 5 moles, per mole of the raw material substituted aromatic compound.

The alkylation of the present invention is characterized by being carried out using only Broensted acid and differs from the conventional method in which the alkylation is performed using, as a catalyst, a combination of a Lewis acid such as a Friedel-Crafts catalyst with a Broensted acid or using a Lewis acid by itself. As described previously, the coexistence of a Lewis acid such as $BF_3$ in the alkylation stage is not desirable because the alkylation is prevented from proceeding.

The alkylation temperature is generally lower than 50° C. but not lower than −30° C., preferably not higher than 20° C.

but not lower than −20° C. An alkylation temperature below 50° C. can prevent the polyalkylation from proceeding and can increase the selectivity of the desired monoalkylated product. Although the temperature below −30° C. does not bring about problems, it is not necessary to excessively perform cooling. During the course of the alkylation, the temperature occasionally temporarily increases due to exotherm. If the temperature is quickly lowered by cooling, such a temporary temperature increase beyond the above temperature range is permissive.

In the above alkylation step, the alkylation selectively occurs at a specific position of the ortho, meta or para position depending upon the effect of the functional group (orientation) on the aromatic ring. For instance, the alkylation of metaxylene with propylene in the presence of an HF catalyst gives mainly 2,4-dimethlcumene.

Next, to the same reaction vessel, a Lewis acid such as $BF_3$ is fed so that isomerization reaction occurs to obtain the compound represented by the general formula (2) as a result of the intramolecular transalkylation (isomerization). The intramolecular isomerization takes place when the Broensted acid and the Lewis acid form a complex with the alkylated aromatic compound. The major product is a positional isomer which is more stable as a complex. Stated otherwise, the major product is an alkyl aromatic compound which has an increased basicity. Thus, the end product having a composition different from the thermodynamically equilibrium composition is obtained. For instance, 2,4-dimethylcumene produced by the alkylation of metaxylene with propylene in the presence of an HF catalyst undergoes an isomerization reaction in the copresence of HF and $BF_3$ to give 3,5-dimethylcumene. The above reaction, such as the alkylation of metaxylene with propylene which results in the formation of 3,5-dimethylcumene, hardly proceeds, when the catalyst used in the isomerization reaction is HF alone or $BF_3$ alone, or when HF and $BF_3$ coexist from the start of the initial alkylation stage.

The amount of $BF_3$ is preferably at least 0.5 mole per mole of the starting aromatic compound. The reaction temperature may be the same as that in the alkylation reaction and generally lower than 50° C. but not lower than −30° C., preferably not higher than 20° C. but not lower than −20° C.

The catalysts HF and $BF_3$ used in the present invention may be separated, recovered and recycled and do not encounter a problem of disposal of waste catalysts which has conventionally involved aluminum chloride. Namely, HF and $BF_3$ after the reaction can be easily separated and recovered by being brought into thermal contact with recirculating hydrocarbons in a distillation column and can be recycled to the reaction system. Since the reaction temperature is so low in the present invention, corrosion of the apparatuses is not caused. Further, since HF and $BF_3$ used in the present invention have a high positional selectivity, the separation and purification of the desired product do not require a separation step by distillation and are easier as compared with the reaction product obtained by using a solid acid or other Lewis acids. Accordingly, the process of the present invention is an economically excellent industrial process.

In the present invention, since a Broensted acid is used in the alkylation reaction and a Lewis acid is used in the isomerization reaction, and, in particular, since HF is used as the Broensted acid and $BF_3$ is used as the Lewis acid, each of the reactions may be carried out in a suitable manner. The above method quite differs from the conventional alkylation by Friedel-Crafts reaction or an improved method thereof.

That is, the process of the present invention is characterized by the use of only Broensted acid for carrying out a step which corresponds to the alkylation in the conventional method and by the formation of a Broensted acid-Lewis acid complex, such as $HF-BF_3$, for carrying out a step which corresponds to an isomerization reaction. Namely, the point in time at which a Lewis acid such as $BF_3$ is added is delayed. Thus, the alkylation using the Broensted acid, such as HF, and the isomerization using the Broensted acid-Lewis acid complex, such as $HF-BF_3$, are allowed to proceed as if the both reactions were a single reaction. Further, the reactions may be performed in "one pot" without removing the catalyst or isolating the product by distillation halfway in the reaction.

As described in the foregoing, the process of the present invention is excellent in the results of the reaction as compared with the conventional method and has a number of advantages in the process steps and, therefore, is clearly distinct from the conventional method.

The present invention will be described in more detail below by way of examples. However, the present invention is not restricted by these examples in any way.

In the examples, the reaction results (yield and selectivity) are values on the basis of propylene unless otherwise specifically noted.

EXAMPLE 1

In a Hastelloy C autoclave having an inside volume of 300 mL and equipped with an electromagnetic stirrer, a baffle plate, a gas blowing port and a liquid feed port, 20 g (0.19 mole) of metaxylene was charged, to which 18.8 g (0.94 mole) of anhydrous HF was slowly fed from the liquid feed port under a pressure. The contents were cooled to −10° C. Next, 7.9 g (0.19 mole) of propylene was gradually fed to the autoclave from the gas blowing port. After the completion of the feed, stirring was started and continued for 30 minutes. Stirring was then stopped and 25.5 g (0.38 mole) of $BF_3$ was gradually introduced into the autoclave from the gas blowing port. The temperature before the $BF_3$ feed was −15° C. After the completion of the $BF_3$ feed, the stirring was again started and continued for 30 minutes. Then, the reaction was terminated. Thereafter, the reaction mixture was poured in an ice water. Extraction was carried out using 80 g of toluene and the organic layer was separated. The aqueous layer was again extracted with 50 g of toluene. The two organic layers were combined and washed with an aqueous sodium hydrogen carbonate solution and then with purified water. The product was analyzed by gas chromatography. The yield of 3,5-dimethylcumene was 64%, and the selectivity was 92%.

EXAMPLE 2

A reaction was carried out using a Hastelloy C autoclave having an inside volume of 6,000 mL and equipped with an electromagnetic stirrer, a baffle plate, a gas blowing port and a liquid feed port in the same manner as that in Example 1. For the reaction, 2,003 g (18.9 moles) of metaxylene, 943 g (47.1 moles) of anhydrous HF and 715 g (17.0 moles) of propylene were used. After the reaction was terminated, the reaction mixture was fed at a rate of 300 mL per hour together with 600 g per hour of benzene to a distillation column (column internal pressure: 0.38 MPa, 122° C.) in which benzene was recirculated. A benzene solution of 3,5-dimethylcumene was separated and collected from the bottom of the column, while discharging $BF_3$ from the top and HF from a discharge port below the condenser. The benzene solution of 3,5-dimethylcumene obtained from the bottom of the column was condensed using an evaporator and then distilled (column internal pressure: 0.0133 MPa, stage number: 12, a reflux ratio:

10) to obtain 1,925 g of desired 3,5-dimethylcumene (distillation temperature: 129° C.). The purity was 99.2% and isolation yield was 76%.

EXAMPLE 3

The reaction of Example 2 was carried out in the same manner. Thereafter, the reaction mixture was fed at a rate of 300 mL per hour together with 600 g per hour of benzene to a distillation column (column internal pressure: 0.49 MPa, 136° C.) in which benzene was recirculated. A benzene solution of 3,5-dimethylcumene was separated and collected from the bottom of the column, while discharging $BF_3$ from the top and HF from a discharge port below the condenser. The benzene solution of 3,5-dimethylcumene obtained from the bottom of the column was condensed using an evaporator and then distilled in the same manner as that in Example 2 to obtain 1,911 g of desired 3,5-dimethylcumene. The purity was 99.0% and isolation yield was 76%.

EXAMPLE 4

The reaction of Example 2 was carried out in the same manner. Thereafter, the reaction mixture was fed at a rate of 140 mL per hour together with 430 g per hour of hexane to a distillation column (column internal pressure: 0.38 MPa, 110° C.) in which hexane was recirculated. A hexane solution of 3,5-dimethylcumene was separated and collected from the bottom of the column, while discharging $BF_3$ from the top and HF from a discharge port below the condenser. The hexane solution of 3,5-dimethylcumene obtained from the bottom of the column was condensed using an evaporator and then distilled in the same manner as that in Example 2 to obtain 1,872 g of desired 3,5-dimethylcumene. The purity was 98.7% and isolation yield was 74%.

EXAMPLE 5

Example 1 was repeated in the same manner as described except that the feed amount of propylene was 4.0 g (0.09 mole). The product obtained was analyzed by gas chromatography to reveal that the yield of desired 3,5-dimethylcumene was 74% and the selectivity was 91%. It is appreciated that the yield is improved by using propylene in an amount of 0.5 mole per mole of metaxylene as compared with the yield (64%) obtained by using propylene in an amount of 1 mole per mole of metaxylene.

EXAMPLE 6

Example 1 was repeated in the same manner as described except that the amount of HF was 9.4 g (0.47 mole) and the amount of $BF_3$ was 12.8 g (0.19 mole). The product obtained was analyzed by gas chromatography to reveal that the yield of desired 3,5-dimethylcumene was 70% and the selectivity was 94%. It is appreciated that the selectivity is improved by using HF and $BF_3$ in amounts of 2.5 moles and 1 mole, respectively, per mole of metaxylene as compared with the selectivity (92%) obtained by using HF and $BF_3$ in amounts of 5 moles and 2 moles, respectively, per mole of metaxylene.

EXAMPLE 7

Example 1 was repeated in the same manner as described except that psudocumene was used in lieu of metaxylene. The product obtained was analyzed by gas chromatography to reveal that the yield of desired 2,3,5-trimethylcumene was 74% based on the psudocumene and the selectivity was 99% based on the psudocumene.

COMPARATIVE EXAMPLE 1

Example 1 was repeated in the same manner as described except that $BF_3$ was added before the feed of propylene. The product obtained was analyzed by gas chromatography to reveal that the yield of desired 3,5-dimethylcumene was 9% and the selectivity was 99%. It is appreciated that, when $BF_3$ is added in the alkylation reaction stage, the yield is considerably low, although the selectivity is high.

COMPARATIVE EXAMPLES 2 to 7

Comparative Example 1 was repeated in the same manner as described except that the amounts of HF and propylene (molar ratios relative to metaxylene) were changed. The yield of 3,5-dimethylcumene and selectivity are shown Table 1.

It is seen that, when $BF_3$ is added in the alkylation reaction stage, good results including the yield and selectivity are not obtained even when the amounts of HF and propylene are changed.

TABLE 1

| | Molar ratio employed | | Reaction results | |
| --- | --- | --- | --- | --- |
| | HF/metaxylene | Propylene/ metaxylene | Yield (%) | Selectivity (%) |
| Comparative Example 2 | 5 | 0.6 | 4 | 58 |
| Comparative Example 3 | 6 | 4 | 45 | 68 |
| Comparative Example 4 | 10 | 4 | 46 | 76 |
| Comparative Example 5 | 5 | 11 | 0 | 0 |
| Comparative Example 6 | 5 | 4 | 19 | 47 |
| Comparative Example 7 | 20 | 4 | 48 | 50 |

COMPARATIVE EXAMPLE 8

Example 1 was repeated in the same manner as described except that $BF_3$ was not added at all. The product obtained was analyzed by gas chromatography to reveal that the yield of desired 3,5-dimethylcumene was 7% and the selectivity was 13% and the yield of 2,4-dimethylcumene was 27%. It is appreciated that, when $BF_3$ is not added, the isomerization does not proceed.

COMPARATIVE EXAMPLE 9

Comparative Example 8 was repeated in the same manner as described except that HF and propylene were used in amounts of 60 g (3.0 moles) and 32 g (0.75 mole), respectively. The product obtained was analyzed by gas chromatography to reveal that the yield of desired 3,5-dimethylcumene was 0.2% and the selectivity was 0.2% and that the yield of 2,4-dimethylcumene was 0.5% and the yield of diisopropyl-metaxylene was 70%. It is appreciated that, when the amounts of HF and propylene increase without using $BF_3$, the yield of di-substituted product considerably increases and the desired product is hardly obtained.

COMPARATIVE EXAMPLE 10

Comparative Example 1 was repeated in the same manner as described except that, after HF, BF$_3$ and propylene had been entirely added, the reaction was performed for 6 hours. The product obtained was analyzed by gas chromatography to reveal that the yield of desired 3,5-dimethylcumene was 1.1% and the selectivity was 27%. The yield of 2,4-dimethylcumene was 0% and the yield of diisopropylmetaxylene was 0.1%. From the fact that the alkylated products are scarcely obtained even when the reaction time is increased, it is seen that the alkylation reaction does not proceed in the presence of BF$_3$, but rather a stable metaxylene/HF/BF$_3$ complex is formed.

COMPARATIVE EXAMPLE 11

Example 1 was repeated in the same manner as described except that HF was not added at all and that the amount of BF$_3$ was changed to 19.2 g (0.28 mole) and the reaction time was changed to 30 minutes because no HF was added. The product obtained was analyzed by gas chromatography to reveal that the yield of desired 3,5-dimethylcumene was 0.9% and the selectivity was 2.4%. It is appreciated that when HF is not added, the alkylation reaction does not proceed.

INDUSTRIAL APPLICABILITY

According to the process of the present invention, in the production of an alkyl aromatic compound which has substituents at the 3- and 5-positions and which generally involves a difficulty in the introduction into the aromatic nucleus, the desired alkyl aromatic compound may be produced with high yield and high selectivity under mild and simple reaction conditions from a raw material aromatic compound.

The alkyl aromatic compounds produced by the process of the present invention are useful as intermediates for functional chemicals for use in pharmaceutical, agricultural and electronic materials.

With the method of the present invention, the catalyst used can be recovered and recycled. Thus, desired alkyl aromatic compounds may be obtained economically in an industrially advantageous manner while reducing the load on the environment.

The invention claimed is:

1. A process for producing an alkyl aromatic compound represented by the general formula (2), characterized in that an aromatic compound represented by the general formula (1) is alkylated with an olefin having 2 to 4 carbon atoms in the presence of a Broensted acid and without the presence of a Lewis acid, and in that the resulting mixture is subsequently added with a Lewis acid and is subjected to isomerization in the copresence of the Broensted acid and the Lewis acid, wherein the temperature at which the reaction of the aromatic compound represented by the general formula (1) with the olefin is performed is not higher than 20° C. but not lower than −20° C., and wherein the Broensted acid is HF and the Lewis acid is BF$_3$

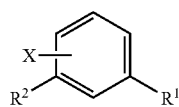
(1)

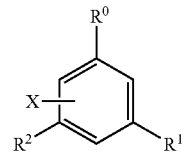
(2)

wherein R$^1$ and R$^2$ are each a methyl group, X represents a hydrogen atom or an alkyl group, and R$^0$ represents an ethyl group, an isopropyl group, a sec-butyl group or a tert-butyl group.

2. A process for producing an alkyl aromatic compound as recited in claim 1, wherein the reaction of the aromatic compound represented by the general formula (1) with the olefin in the presence of a Broensted acid is performed with a molar ratio of the Broensted acid to the aromatic compound being 1 or more.

3. A process for producing an alkyl aromatic compound as recited in claim 1, wherein the isomerization in the copresence of the Lewis acid and the Broensted acid after the reaction of the aromatic compound represented by the general formula (1) with the olefin in the presence of a Broensted acid is performed with a molar ratio of the Lewis acid to the aromatic compound represented by the general formula (1) being 0.5 or more.

4. A process for producing an alkyl aromatic compound as recited in claim 1, wherein the isomerization in the copresence of the Lewis acid and the Broensted acid after the reaction of the aromatic compound represented by the general formula (1) with the olefin in the presence of a Broensted acid is performed at a temperature lower than 50° C. but not lower than −30° C.

5. A process for producing an alkyl aromatic compound as recited in claim 1, wherein the olefin having 2 to 4 carbon atoms is selected from the group consisting of ethylene, propylene, butylenes and isobutylene.

6. A process for producing an alkyl aromatic compound as recited in claim 1, wherein X is a hydrogen atom in the general formulas (1) and (2), and wherein R$^0$ is an isopropyl group in the general formula (2).

7. A process for producing an alkyl aromatic compound as recited in claim 3, wherein the isomerization in the copresence of the Lewis acid and the Broensted acid after the reaction of the aromatic compound represented by the general formula (1) with the olefin in the presence of a Broensted acid is performed at a temperature lower than 50° C. but not lower than −30° C.

8. A process for producing an alkyl aromatic compound as recited in claim 7, wherein the olefin having 2 to 4 carbon atoms is selected from the group consisting of ethylene, propylene, butylenes and isobutylene.

9. A process for producing an alkyl aromatic compound as recited in claim 8, wherein X is a hydrogen atom in the general formulas (1) and (2), and wherein R$^0$ is an isopropyl group in the general formula (2).

10. A process for producing an alkyl aromatic compound as recited in claim 2, wherein said molar ratio of the Broensted acid to the aromatic compound is 2 to 5.

11. A process for producing an alkyl aromatic compound as recited in claim 1, wherein the olefin is included in an amount of 0.5 to 1 mole per mole of the aromatic compound.

12. A process for producing an alkyl aromatic compound as recited in claim 1, wherein said isomerization is performed at a temperature not higher than 20° C. but not lower than −20° C.

13. A process for producing an alkyl aromatic compound as recited in claim 4, wherein said isomerization is performed at a temperature not higher than 20° C. but not lower than −20° C.

14. A process for producing an alkyl aromatic compound as recited in claim 1, wherein the alkylation and the isomerization are carried out in a same single reaction chamber.

15. A process for producing an alkyl aromatic compound as recited in claim 1, wherein X is a methyl group.

* * * * *